United States Patent [19]
Infinger

[11] Patent Number: 5,527,345
[45] Date of Patent: Jun. 18, 1996

[54] IMPLANTABLE ATRIAL DEFIBRILLATOR HAVING AN INTERMITTENLY ACTIVATED PACING MODALITY

[76] Inventor: Kenneth R. Infinger, 22224 NE. 21st Way, Redmond, Wash. 98053

[21] Appl. No.: 243,858

[22] Filed: May 17, 1994

[51] Int. Cl.$^6$ .................................................. A61N 1/39
[52] U.S. Cl. ................................................ 607/4; 607/16
[58] Field of Search .................................... 607/16, 4, 5, 9

[56] References Cited

U.S. PATENT DOCUMENTS

| | | | |
|---|---|---|---|
| 4,404,972 | 9/1983 | Gordon et al. | 607/16 |
| 4,693,253 | 9/1987 | Adams | 607/4 |
| 4,860,751 | 8/1989 | Callaghan | 607/16 |
| 5,265,600 | 11/1993 | Adams et al. | 607/4 |

FOREIGN PATENT DOCUMENTS

| 3218733 | 12/1982 | Germany | 607/16 |
|---|---|---|---|

*Primary Examiner*—William E. Kamm
*Assistant Examiner*—Kennedy J. Schaetzle
*Attorney, Agent, or Firm*—Richard O. Gray, Jr.

[57] ABSTRACT

An implantable atrial defibrillator applies cardioverting electrical energy to the atria of a human heart in need of cardioversion and thereafter paces the heart in a demand mode. The atrial defibrillator includes a first detector for detecting atrial activity of the heart, an atrial fibrillation detector responsive to the atrial activity detected by the first detector for determining when the atria of the heart are in need of cardioversion, and a cardiovertor responsive to the atrial fibrillation detector for applying the cardioverting electrical energy to the atria of the heart when the atria are in need of cardioversion. The defibrillator further includes a pacer for pacing the heart in a demand mode, a depletable power source for providing electrical power to the first detector, the atrial fibrillation detector, the cardiovertor, and the pacer, and an enable/disable stage for enabling the pacer in response to the cardiovertor applying the cardioverting electrical energy to the atria and thereafter disabling the pacer in response to the occurrence of a predetermined event for conserving the depletable power source.

11 Claims, 1 Drawing Sheet

IMPLANTABLE ATRIAL DEFIBRILLATOR HAVING AN INTERMITTENLY ACTIVATED PACING MODALITY

BACKGROUND OF THE INVENTION

The present invention generally relates to an automatic implantable atrial defibrillator for delivering cardioverting or defibrillating electrical energy to the atria of a human heart. The present invention is more particularly directed to such an atrial defibrillator which has an intermittently activated pacing modality for assisting the heart in returning to normal sinus rhythm immediately following each attempted cardioversion of the atria. Because the pacing function is only activated for a finite period of time following each attempted cardioversion, the pacing function is provided without undue power consumption of a depletable power source, such as a battery, within the atrial defibrillator.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has been the cause of these defibrillators from becoming a commercial reality. Two such defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Implantable ventricular defibrillators for applying defibrillating electrical energy to the ventricles of the heart are well known and have been commercially available for a number of years. Because ventricular fibrillation is life threatening, resulting in unconsciousness in just a few seconds and leading to death in just a few minutes, implantable ventricular defibrillators are fully automatic for detecting ventricular fibrillation and quickly applying the defibrillating electrical energy to the ventricles. Such defibrillators are quite large in physical size as compared to the size of a pacemaker, for example, because of the rather large battery and storage capacitors required for providing defibrillating energies of ten joules of more. Due to their rather large size, these devices must be implanted in an abdominal region of the human body.

Any form of implantable device must be powered by a portable, depletable power source, such as a battery. When the battery is depleted of its energy, it is necessary to explant the device and implant a replacement. As a result, for an implantable device to be considered commercially viable, it is generally believed that the device should have a predicted lifetime of a number of years, such as five years, for example.

Predicted lifetimes of less than five years for ventricular defibrillators have not diminished the commercial nature of these devices because ventricular fibrillation is life threatening. However, since atrial fibrillation is not generally considered to be life threatening, it is generally believed that atrial defibrillators should have lifetimes on the order of five years to render such devices commercial in nature. To further enhance the commercial nature of these devices, it is desirable to limit the physical size of an atrial defibrillator to the size of a large pacemaker, for example, to permit the atrial defibrillator to be implanted, like a pacemaker, within the chest of the human body. While predicted lifetime and physical size have not adversely affected the commercial nature of ventricular defibrillators, such constraints have probably been the cause of an atrial defibrillator not being commercially available to date.

It has long been believed that as much electrical energy is required to cardiovert or defibrillate the atria of the heart as is required to cardiovert or defibrillate the ventricles of the heart, on the order of ten joules or more. Furthermore, episodes of atrial fibrillation occur much more frequently than do episodes of ventricular fibrillation. As a result, due to the contemplated required cardioverting or defibrillating energy levels for cardioverting or defibrillating the atria of the heart and the predicted required frequency of delivering such energies, it has long been believed that an implantable atrial defibrillator would either have an unreasonably short and commercially unacceptable predicted lifetime or a battery and storage capacitor of such a large size that the atrial defibrillator would be too large in physical size. Fortunately, a lead system has been discovered for an atrial defibrillator which greatly reduces the amount of energy required to defibrillate or cardiovert the atria. This lead system is fully described in U.S. Pat. No. 5,279,291 which issued on Jan. 18, 1994 for "Method for Atrial Defibrillation" which is assigned to the assignee of the present invention, and which is incorporated herein by reference. The lead system described in that patent includes a first electrode in the coronary sinus or great cardiac vein of the heart and a second electrode in the right atrium or superior vena cava of the heart. With such electrode placement, cardioverting energy applied to these electrodes is substantially confined to the atria, reducing the amount of energy required to cardiovert the atria to on the order of one joule or less.

It has also long been believed that an atrial defibrillator, like a ventricular defibrillator, should charge its storage capacitor quickly to permit essentially immediate cardioversion. Such quick storage capacitor charging places an extreme drain on the battery thereby further limiting the predicted lifetime of an implantable atrial defibrillator and further adding to the heretofore perceived non-commercial nature of these devices.

Recently, it has been recognized that, since atrial fibrillation is not life threatening, the storage capacitor of an atrial defibrillator need not be charged as quickly as the storage capacitor of a ventricular defibrillator. That recognition has led to another improvement in an atrial defibrillator fully described in U.S. Pat. No. 5,251,624 for "Pulse Generator for Use in an Implantable Atrial Defibrillator" which issued on Oct. 12, 1993, which is assigned to the assignee of the present invention and which is also incorporated herein by reference. The pulse generator described in that patent conserves battery power while still providing adequate electrical energy to cardiovert or defibrillate the atria of the heart to arrest atrial fibrillation. This is achieved by charging the storage capacitor comparatively slowly to minimize drain on the defibrillator battery but in sufficient time to arrest the atrial fibrillation. In accordance with the described preferred embodiment, this is accomplished by converting the rather low voltage of the battery to a pulsating high voltage of 300 to 400 volts, for example, with a flyback transformer having a primary winding coupled to an oscillator which provides the primary winding with a high frequency, low duty cycle input. By virtue of this arrangement, sufficient electrical energy for cardioverting or defibrillating the heart is stored in the storage capacitor without imposing a high drain on the defibrillator battery. Even though a minute may be required to fully charge the storage capacitor, this is sufficient to arrest the atrial fibrillation and bring comfort to the patient.

Further, as is well known in the art, the sinus node of the heart is the normal pacemaker of the heart and may be rendered dysfunctional by the application of cardioverting electrical energy to the atria. When such sinus node dysfunction occurs following an attempted cardioversion, the heart is caused to pause for a few seconds. It is also known that patients who suffer from atrial fibrillation may have an increased risk of sinus node dysfunction due to disease and/or drug therapy. Hence, it has been proposed in the past to provide an implantable atrial defibrillator with a demand ventricular pacing modality for pacing the ventricles when required.

Unfortunately, demand pacing requires the maintenance of a pacing output in readiness for pacing and the sensing of heart activity, and more particularly, R waves of the heart. This sensing is generally provided by one or more sense amplifiers and at least one R wave detector.

While sense amplifiers and R wave detectors used to sense heart activity and pacer output circuits are generally perceived as consuming little power when held in a fully biased readiness condition, the power consumed by these circuits under such conditions in a continuous manner over periods of months and years as is contemplated by the prior art, is considerable. Hence, the power consumed by continuously maintaining a demand pacing modality of an implantable atrial defibrillator in readiness is still another factor which limits the predicted lifetimes of these devices.

The present invention overcomes the power consumption problem of maintaining continuous demand pacing readiness in a fully automatic atrial defibrillator. This is accomplished by effectively providing power to the pacing circuitry for only a short finite time period following each attempted cardioversion. As a result, demand pacing is provided during those times when sinus node dysfunction may be present while conserving precious battery power. In fact, by practicing the present invention as described hereinafter, a twenty percent (20%) savings in battery power may be realized.

SUMMARY OF THE INVENTION

The present invention provides an implantable atrial defibrillator for applying cardioverting electrical energy to the atria of a human heart in need of cardioversion and thereafter pacing the heart in a demand mode. The atrial defibrillator includes first detecting means for detecting atrial activity of the heart, atrial fibrillation detecting means responsive to the atrial activity detected by the first detecting means for determining when the atria of the heart are in need of cardioversion, and cardioverting means responsive to the atrial fibrillation detecting means for applying the cardioverting electrical energy to the atria of the heart when the atria are in need of cardioversion. The atrial defibrillator further includes pacing means for pacing the heart in a demand mode, depletable power source means for providing electrical power to the first detecting means, the atrial fibrillation detecting means, the cardioverting means, and the pacing means, and means for enabling the pacing means in response to the cardioverting means applying cardioverting electrical energy to the atria and thereafter disabling the pacing means in response to the occurrence of a predetermined event for conserving the depletable power source means.

The present invention further provides a method for use in an implantable atria defibrillator including a depletable power source for applying cardioverting electrical energy to the atria of a human heart in need of cardioversion and thereafter pacing the heart in a demand mode. The method includes the steps of detecting atrial activity of the heart, determining responsive to the detected atrial activity of the heart if the atria are in fibrillation, and applying cardioverting electrical energy to the atria of the heart if the atria are in fibrillation. The method includes the further steps of providing pacing means for pacing the heart in a demand mode, enabling the pacing means in response to applying cardioverting electrical energy to the atria of the heart, and disabling the pacing means in response to the occurrence of a predetermined event for conserving the depletable power source.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole FIGURE of which like reference numerals identify identical elements, and wherein the sole FIGURE is a block diagram of a fully implantable atrial defibrillator embodying the present invention.

DETAILED DESCRIPTION OF THE PREFERRED EMBODIMENT

Figure 1:
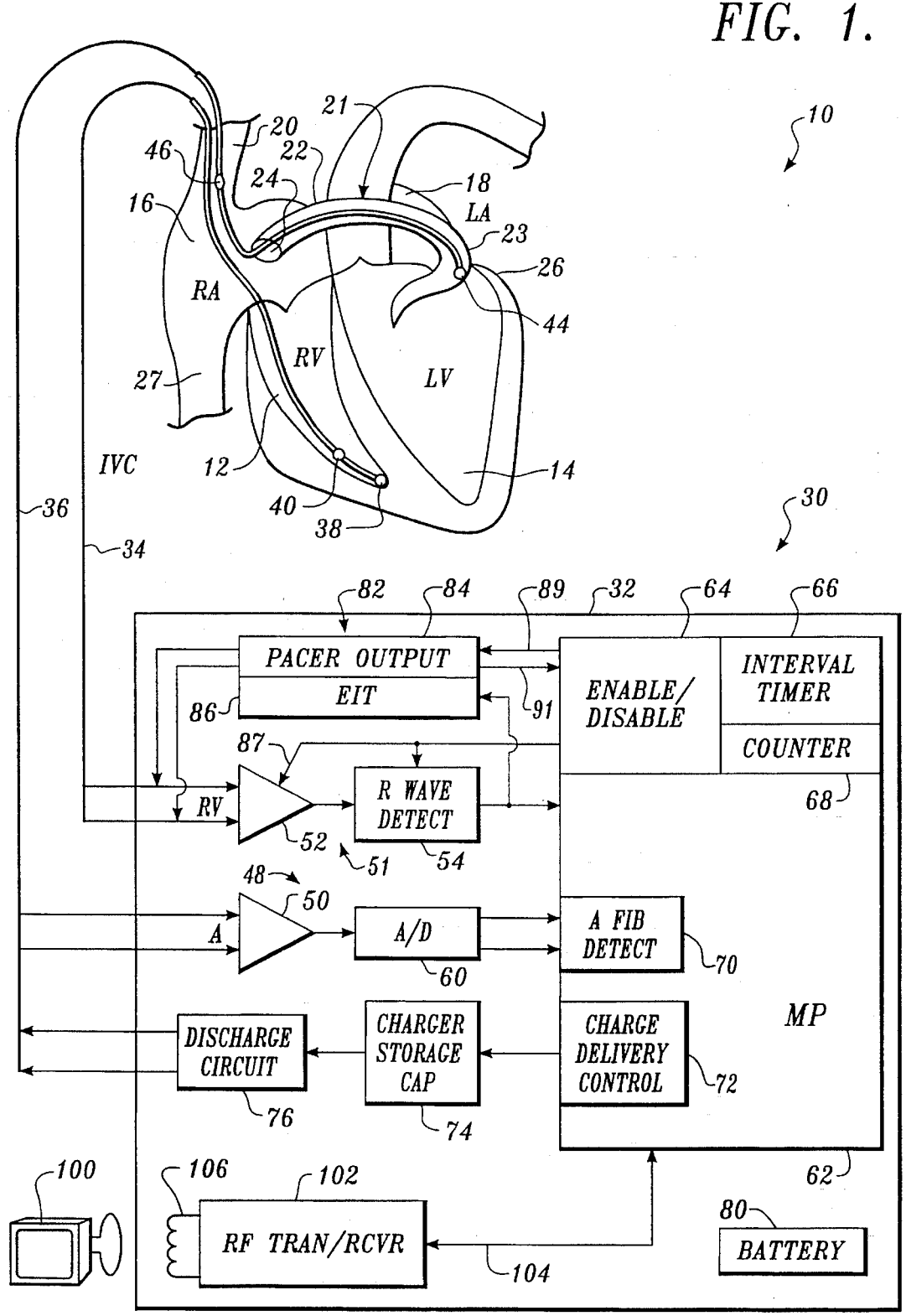

Referring now to the sole FIGURE, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in the sole FIGURE are the right ventricle 12, the left ventricle 14, the right atrium 16, the left atrium 18, the superior vena cava 20, the coronary sinus channel 21, which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular activations in the right ventricle. The electrodes 38 and 40 further provide for pacing the ventricles 12 and 14 in a manner to be described hereinafter in accordance with the present invention. As illustrated, the lead 34 is fed through the superior vena cava 20, into the right atrium 16, and then into the right ventricle 12.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, a second sense amplifier 52, and an R wave detector 54. The first sense amplifier 50 forms a first detecting means 48 which, together with the lead 36 to which sense amplifier 50 is coupled, senses atrial activity of the heart. The second sense amplifier 52 and the R wave detector 54 form a second detecting means 51 which, together with the lead 34 to which sense amplifier 52 is coupled, detects ventricular activations of the right ventricle of the heart.

The output of the second sense amplifier 52 is coupled to the R wave detector 54. The R wave detector 54 is of the type well known in the art which provides an output pulse upon the occurrence of an R wave being sensed during a cardiac cycle of the heart.

The output of the first sense amplifier 50 is coupled to an analog to digital converter 60. The analog to digital converter 60 converts the analog signal representative of the atrial activity of the heart being detected to digital samples for further processing in a manner to be described hereinafter.

The enclosure 32 of the atrial defibrillator 30 further includes a microprocessor 62. The implementation of the microprocessor 62 in accordance with this embodiment of the present invention results in a plurality of functional stages. The stages include an enable/disable stage 64, an interval timer stage 66, a counter stage 68, an atrial arrhythmia detector in the form of an atrial fibrillation detector 70, and a charge delivery and energy control stage 72.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and conveys the data to the memory over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, the microprocessor 62 receives such programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in internal memory or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32.

To complete the identification of the various structural elements within the enclosure 32, the atrial defibrillator 30 further includes a charger and storage capacitor circuit 74 of the type well known in the art which charges a storage capacitor to a predetermined voltage level, a discharge circuit 76 for discharging the storage capacitor within circuit 74 during a predetermined discharge time to provide a controlled discharge output of electrical energy, when required, to the atria of the heart, and a pacer 82 for applying pacing electrical energy to the ventricles of the heart.

The discharge circuit 76 is coupled to the first electrode 44 and the second electrode 46 of the second lead 36. This permits the application of the cardioverting or defibrillating electrical energy to the atria.

The pacer 82 may be of the type well known in the art for providing pacing electrical energy to the right ventricle 12 in a demand mode. The pacer 82 includes an output circuit 84 which is coupled to electrodes 38 and 40 of lead 34 for applying the pacing electrical energy to the right ventricle 12. The pacer 82 further includes an escape interval timer 86 for timing an escape interval to permit the pacer 82 to operate in a demand mode as well known in the art. The pacer also utilizes, and hence includes, the sense amplifier 52 and R wave detector 54 for sensing activity of the right ventricle and resetting the escape interval timer 86 when an R wave is detected within a timed escape interval.

Lastly, the defibrillator 30 includes a depletable power source 80, such a lithium battery. The battery 80 provides power to the electrical components of the atrial defibrillator 30.

At spaced apart times, as for example every 5 to 20 minutes, the microprocessor 62 enables the sense amplifier 52 and R wave detector 54, over control line 87 and sense amplifier 50 and the analog to digital converter 60 to acquire data representative of the activity of the heart which is stored in the aforementioned memory (not shown).

The atrial fibrillation detector 70 then processes the stored data to determine if the heart is experiencing an episode of atrial fibrillation. If atrial fibrillation is detected, the charge delivery and control stage 72 initiates the storage of the cardioverting electrical energy within the storage capacitor of charger and storage capacitor circuit 74. When the storage capacitor is fully charged, the microprocessor then preferably initiates a safety protocol as fully described in U.S. Pat. No. 5,207,219 which issued on May 4, 1993 for Atrial Defibrillator and Method For Providing Interval Timing Prior to Cardioversion, which patent is assigned to the assignee of the present invention and incorporated herein by reference. As described in that patent, the microprocessor 62 times the time between successively detected R waves to time the cardiac intervals of the heart. When a cardiac interval is timed which exceeds a predetermined minimum time interval, the microprocessor 62, through the discharge circuit 76, discharges the storage capacitor of circuit 74 for a predetermined discharge time to apply cardioverting electrical energy to electrodes 44 and 46 of lead 36. This applies the cardioverting electrical energy to the atria 16 and 18 of the heart for cardioverting the atria.

After applying the cardioverting electrical energy to the atria, the microprocessor 62, through the enable/disable stage 64, enables the pacer output 84 and escape interval timer 86 over control line 89. This begins the post-cardioversion demand pacing of the heart. Pacing of the heart is enabled for a finite time until the occurrence of a predetermined event.

In accordance with a first embodiment of the present invention, the predetermined event may be the completion of a timing interval. To that end, the interval timer 66 may be utilized for timing a time interval beginning immediately after each cardioversion attempt and extending for a time of, for example, 15 seconds to five minutes, and preferably one minute. When the timer 66 completes the timing of the predetermined time interval, the enable/disable stage 64 then disables the pacer 82 by disabling the pacer output 84 and escape interval timer 86 over control line 89 and disabling the sense amplifier 52 and R wave detector 54 over control line 87.

Alternatively, and in accordance with a second embodiment of the present invention, the predetermined event may be the completion of a predetermined number of cardiac cycles. To that end, the counter 68 counts the intrinsic or natural R waves of the heart and the pacing pulses issued by the pacer output 84 for counting the cardiac cycles of the heart occurring since the attempted cardioversion. When the counter 68 has counted a predetermined number of cardiac cycles, for example between 15 and 300 cardiac cycles, and preferably 30 cardiac cycles, the enable/disable stage 64 then disables the pacer output 84 and the escape interval timer 86 over control line 89 and the sense amplifier 52 and the R wave detector 54 over control line 87 as previously described.

Most preferably, and in accordance with a third embodiment of the present invention, the predetermined event is the occurrence of a consecutive number of intrinsic cardiac cycles of the heart. Here again, the counter 68 is utilized but for counting only intrinsic R waves of the heart detected by the sense amplifier 52 and the R wave detector 54. When the pacer output 84 paces the heart, the pacer output 84 provides a reset signal over reset line 91 to reset the counter 68. As a result, the count in counter 68 will represent the last number of consecutive intrinsic or natural cardiac cycles of the heart. When the count in counter 68 reaches a predetermined count, as for example between three and ten intrinsic cardiac cycles, and preferably three intrinsic cardiac cycles, indicating that the predetermined number of consecutive intrinsic cardiac cycles have occurred, the enable/disable stage 64 then disables the pacer output 84 and escape interval timer 86 over control line 89 and disables the sense amplifier 52 and R wave detector 54 over control line 87.

For enabling and disabling the pacer 82, the bias voltage on the pacer output 84, escape interval timer 86, sense amplifier 52 and R wave detector 54 may be switched between a low bias voltage, rendering these circuits disabled and inoperative, to a regular bias voltage, to effectively provide power to these circuits for rendering these circuits enabled and fully operative. In the disabled state, these circuits would consume little if any measurable power to conserve the battery 80.

Alternatively, a solid state switch may be employed between the battery 80 and each of the pacer output 84, the escape interval timer 86, the sense amplifier 52, and the R wave detector 54. When the pacer 82 is disabled, the control lines 87 and 89 will turn the solid state switches off to effectively disconnect these circuits from the battery. When these circuits are enabled, the control lines 87 and 89 will turn the solid state switches on to connect the circuits to the battery. When the pacer is disabled, only the leakage current through the solid state switches will consume power.

Unlike the prior art which contemplates continuous enablement of demand pacing, the atrial defibrillator of the present invention enables demand pacing during only a finite time period following each attempted cardioversion. Hence, not only does the present invention provide an atrial defibrillator which provides demand pacing during the time when sinus node dysfunction may be present, in addition, it does so in a manner which conserves precious battery power. In fact, by practicing the present invention, a twenty percent (20%) savings in battery power may be realized.

While a particular embodiment of the present invention has been shown and described, modifications may be made, and it is therefore intended to cover in the appended claims all such changes and modifications which fall within the true spirit and scope of the invention.

What is claimed is:

1. An implantable atrial defibrillator for applying cardioverting electrical energy to the atria of a human heart in need of cardioversion and thereafter pacing the heart in a demand mode, said atrial defibrillator comprising:

first detecting means for detecting atrial activity of the heart;

atrial fibrillation detecting means responsive to the atrial activity detected by said first detecting means for determining when the atria of the heart are in need of cardioversion;

cardioverting means responsive to said atrial fibrillation detecting means for applying the cardioverting electrical energy to the atria of the heart when the atria are in need of cardioversion;

pacing means for pacing the heart in a demand mode;

depletable power source means for providing electrical power to said first detecting means, said atrial fibrillation detecting means said cardioverting means, and said pacing means; and means for enabling said pacing means in response to said cardioverting means applying said cardioverting electrical energy to the atria and thereafter disabling said pacing means in response to the occurrence of a predetermined event for conserving said depletable power source means, said pacing means including a pacing output for applying pacing electrical energy to the heart and sensing means for sensing activity of the heart and wherein said means for enabling and disabling enables and disables said pacing output and said sensing means.

2. An atrial defibrillator as defined in claim 1 further including a timer for timing a time interval responsive to said cardioverting means applying said cardioverting electrical energy and wherein said means for enabling and disabling is responsive to said timer timing said time interval for disabling said pacing means.

3. An implantable atrial defibrillator for applying cardioverting electrical energy to the atria of a human heart in need of cardioversion and thereafter pacing the heart in a demand mode, said atrial defibrillator comprising:

first detecting means for detecting atrial activity of the heart;

atrial fibrillation detecting means responsive to the atrial activity detected by said first detecting means for determining when the atria of the heart are in need of cardioversion;

cardioverting means responsive to said atrial fibrillation detecting means for applying the cardioverting electrical energy to the atria of the heart when the atria are in need of cardioversion;

pacing means for pacing the heart in a demand mode;

depletable power source means for providing electrical power to said first detecting means, said atrial fibrillation detecting means, said cardioverting means, and said pacing means;

means for enabling said pacing means in response to said cardioverting means applying said cardioverting electrical energy to the atria and thereafter disabling said pacing means in response to the occurrence of a predetermined event for conserving said depletable power source means;

counting means for counting cardiac cycles of the heart responsive to said cardioverting means applying said cardioverting electrical energy, and said means for enabling and disabling being responsive to said counting means counting a predetermined number of cardiac cycles of the heart for disabling said pacing means.

4. An implantable atrial defibrillator for applying cardioverting electrical energy to the atria of a human heart in need of cardioversion and thereafter pacing the heart in a demand mode, said atrial defibrillator comprising:

first detecting means for detecting atrial activity of the heart;

atrial fibrillation detecting means responsive to the atrial activity detected by said first detecting means for determining when the atrial of the heart are in need of cardioversion;

cardioverting means responsive to said atrial fibrillation detecting means for applying the cardioverting electrical energy to the atria of the heart when the atria are in need of cardioversion;

pacing means for pacing the heart in a demand mode;

depletable power source means for providing electrical power to said first detecting means, said atrial fibrillation detecting means, said cardioverting means, and said pacing means;

means for enabling said pacing means in response to said cardioverting means applying said cardioverting electrical energy to the atria and thereafter disabling said pacing means in response to the occurrence of a predetermined event for conserving said depletable power source means;

counting means for counting intrinsic cardiac cycles of the heart responsive to said cardioverting means applying said cardioverting electrical energy, and said means for enabling and disabling being responsive to said counting means counting a predetermined number of consecutive intrinsic cardiac cycles of the heart for disabling said pacing means.

5. An atrial defibrillator as defined in claim 4 wherein said pacing means includes reset means for resetting said counting means when said pacing means paces the heart.

6. An atrial defibrillator as defined in claim 4 wherein said predetermined number of consecutive intrinsic cardiac cycles is from three intrinsic cardiac cycles to ten intrinsic cardiac cycles.

7. In an implantable atrial defibrillator including a depletable power source, a method of applying cardioverting electrical energy the atria of a human heart in need of cardioversion and thereafter pacing the heart in a demand mode, said method comprising the steps of:

detecting atrial activity of the heart;

determining responsive to the detected atrial activity of the heart if the atria are in fibrillation;

applying cardioverting electrical energy to the atria of the heart if the atria are in fibrillation;

providing pacing means for pacing the heart in a demand mode;

enabling said pacing means in response to applying cardioverting electrical energy to the atria of the heart; and disabling said pacing means in response to the occurrence of a predetermined event for conserving said depletable power source, said disabling step including timing a time interval upon applying said cardioverting electrical energy and disabling said pacing means when the timing of said time interval is completed.

8. In an implantable atria defibrillator including a depletable power source, a method of applying cardioverting electrical energy to the atria of a human heart in need of cardioversion and thereafter pacing the heart in a demand mode, said method comprising the steps of:

detecting atrial activity of the heart;

determining responsive to the detected atrial activity of the heart if the atria are in fibrillation;

applying cardioverting electrical energy to the atria of the heart if the atria are in fibrillation;

providing pacing means for pacing the heart in a demand mode;

enabling said pacing means in response to applying cardioverting electrical energy to the atria of the heart; and disabling said pacing means in response to the occurrence of a predetermined event for conserving said depletable power source, said disabling step including counting cardiac cycles of the heart upon applying said cardioverting electrical energy and disabling said pacing means when a predetermined number of cardiac cycles have been counted.

9. In an implantable atria defibrillator including a depletable power source, a method of applying cardioverting electrical energy to the atria of a human heart in need of cardioversion and thereafter pacing the heart in a demand mode, said method comprising the steps of:

detecting atrial activity of the heart;

determining responsive to the detected atrial activity of the heart if the atria are in fibrillation;

applying cardioverting electrical energy to the atria of the heart if the atria are in fibrillation;

providing pacing means for pacing the heart in a demand mode;

enabling said pacing means in response to applying cardioverting electrical energy to the atria of the heart; and disabling said pacing means in response to the occurrence of a predetermined event for conserving said depletable power source, said disabling step including counting intrinsic cardiac cycles of the heart upon applying said cardioverting electrical energy and disabling said pacing means when a predetermined number of consecutive intrinsic cardiac cycles have been counted.

10. A method as defined in claim 9 including the further step of providing a counter for counting said intrinsic cardiac cycles and resetting said counter upon pacing the heart.

11. A method as defined in claim 9 wherein said predetermined number of consecutive intrinsic cardiac cycles is from three intrinsic cardiac cycles to ten intrinsic cardiac cycles.

* * * * *

UNITED STATES PATENT AND TRADEMARK OFFICE
CERTIFICATE OF CORRECTION

PATENT NO. : 5,527,345
DATED      : June 18, 1996
INVENTOR(S) : Kenneth R. Infinger It is certified that error appears in the above-indentified patent and that said Letters Patent is hereby corrected as shown below:

On the title page, item [54] and column 1, line 2, "INTERMITTENLY" should be --INTERMITTENTLY--

Column 2, line 48, insert "," after --Defibrillation--

Signed and Sealed this

First Day of October, 1996

Attest:

BRUCE LEHMAN

Attesting Officer

Commissioner of Patents and Trademarks